US012636505B2

(12) United States Patent
McIntosh et al.

(10) Patent No.: US 12,636,505 B2
(45) Date of Patent: May 26, 2026

(54) SYSTEM FOR NEUROLOGICAL STIMULATION

(71) Applicant: BIOTRONIK SE & Co. KG, Berlin (DE)

(72) Inventors: David McIntosh, Wilsonville, OR (US); Greg Pearce, Milwaukie, OR (US); Warren Dabney, Lake Oswego, OR (US); Allan M. Call, Newberg, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 299 days.

(21) Appl. No.: 18/284,776

(22) PCT Filed: Mar. 23, 2022

(86) PCT No.: PCT/EP2022/057638
§ 371 (c)(1),
(2) Date: Sep. 28, 2023

(87) PCT Pub. No.: WO2022/207429
PCT Pub. Date: Oct. 6, 2022

(65) Prior Publication Data
US 2025/0073474 A1 Mar. 6, 2025

Related U.S. Application Data

(60) Provisional application No. 63/168,610, filed on Mar. 31, 2021.

(30) Foreign Application Priority Data

May 5, 2021 (EP) ..................................... 21172200

(51) Int. Cl.
*A61N 1/375* (2006.01)

(52) U.S. Cl.
CPC .................................. *A61N 1/3752* (2013.01)

(58) Field of Classification Search
None
See application file for complete search history.

(56) References Cited

U.S. PATENT DOCUMENTS

| | | | |
|---|---|---|---|
| 6,609,029 B1 * | 8/2003 | Mann | A61N 1/3752 |
| | | | 607/37 |
| 2003/0077943 A1 * | 4/2003 | Osypka | H01R 31/02 |
| | | | 439/623 |

(Continued)

FOREIGN PATENT DOCUMENTS

WO WO 2005/077453 A2 8/2005

OTHER PUBLICATIONS

International Search Report and Written Opinion dated Jul. 6, 2022, for International Application No. PCT/EP2022/057638, 13 pages.

*Primary Examiner* — Erica S Lee
(74) *Attorney, Agent, or Firm* — FBT GIBBONS LLP

(57) ABSTRACT

A system used for neurological stimulation, includes a pulse generator module, including a first housing configured to accommodate a pulse generator unit. The first housing includes a coupling portion and a first electrical interface located at the coupling portion. The pulse generator unit is configured to generate neurological stimulation pulses to be supplied to at least one neurological stimulation electrode via the first electrical interface. A first lead interface module is connectable to the coupling portion and the first electrical interface. The first lead interface module is detachably connectable to the at least one neurological stimulation electrode. A second lead interface module is connectable to the coupling portion and the first electrical interface. The second lead interface module includes an extension cable connectable to an electrode coupling box for supplying (Continued)

neurological stimulation pulses generated by the pulse generator unit to the at least one neurological stimulation electrode.

20 Claims, 10 Drawing Sheets

(56)  References Cited

U.S. PATENT DOCUMENTS

| | | | | |
|---|---|---|---|---|
| 2006/0167522 | A1* | 7/2006 | Malinowski | A61N 1/3752 |
| | | | | 607/37 |
| 2010/0331924 | A1* | 12/2010 | North | A61N 1/3754 |
| | | | | 439/660 |
| 2014/0207205 | A1* | 7/2014 | Jullien | H01R 13/514 |
| | | | | 607/17 |
| 2017/0065813 | A1* | 3/2017 | Chen | A61N 1/3752 |
| 2017/0072189 | A1* | 3/2017 | Janzig | H01R 13/187 |
| 2017/0182326 | A1* | 6/2017 | Bornzin | A61N 1/3752 |
| 2021/0085975 | A1 | 3/2021 | McIntosh et al. | |

* cited by examiner

140

14

14

700'

142

144

146

10,12

134b

144

10,12

14

10,12

10,12

14

SYSTEM FOR NEUROLOGICAL STIMULATION

Embodiments of the present disclosure relate to a system for neurological stimulation. Embodiments of the present disclosure relate more particularly to a compact and reusable system for spinal cord stimulation.

A spinal cord stimulator is a type of implantable neuromodulation device configured to send electrical stimulation pulses to areas of the spinal cord for the treatment of pain conditions. A spinal cord stimulator is a consideration for people who have a pain condition that has not responded to more conservative therapy.

Spinal cord stimulation therapies are not effective for all patients. Prior to receiving a permanent implant, it is common practice to utilize a screening approach to evaluate which patients respond to therapy. The screening consists of two phases: intraoperative testing and patient-worn trialing.

Intraoperative testing is an acute evaluation of the lead integrity and adequacy of lead positioning while in a surgical setting. An external pulse generator (EPG), an intraoperative test cable and an external lead adapter are used to perform the intraoperative testing. The external lead adapter and mated intraoperative test cable connects the external pulse generator to the leads, while at the same time allowing the external pulse generator to remain outside of the surgical sterile field. Intraoperative testing is performed during the placement of the temporary leads (for a trial) and permanent leads (for permanent implant). The external lead adapter is continued to be used to interface to the leads in patient-worn trialing, described below.

For patient-worn trialing, the external pulse generator and mated external lead adapter are affixed via dressings to the patient. The external pulse generator is affixed to the patient for a trial consisting between 3-30 days, with most trials not exceeding 7 days in the United States of America. The patient continues to wear the trial stimulator during normal daily activities. During this time a remote device is used to adjust therapy and to collect patient input feedback related to pain relief (e.g. surveys). Meanwhile, the external pulse generator autonomously collects statistics related to stimulation therapy usage patterns. These statistics are telemetered from the external pulse generator to the remote device e.g. via Bluetooth.

These trial simulators are intended for single use and a single purpose. Therefore, the trials are expensive. In addition, the known trial simulators have electrical connectors that require to increase device size. However, for patient comfort, it is important to keep the trial simulator size small.

US 2021/0085975 A1 describes an adapter system for connecting implantable electrode leads. The adapter system has a pulse generator configured to generate electrical stimulation pulses and has a first connector member. The adapter has a housing containing two receptacles. Each receptacle receives an end portion of an electrode lead to establish an electrical connection between the adapter and the electrode lead. The adapter contains a second connector member configured to engage with the first connector member to establish a mechanical connection between the housing and the pulse generator and an electrical connection between the pulse generator and the electrode lead. A test cable electrically connects the pulse generator to the electrode leads for testing the electrode leads. The test cable contains a first connector member configured to engage with the second connector member to establish an electrical connection. The test cable contains a second connector member configured to engage with the first connector member.

In light of the above, a system for neurological stimulation is provided that overcomes at least some of the problems in the art.

It is an object of the present disclosure to provide a system for neurological stimulation which is reusable and/or reduces costs of spinal cord stimulation therapies. It is another object of the present disclosure to improve patient comfort.

It is an object of the present disclosure to provide a system for neurological stimulation which is easy to manufacture, practical to use and robust.

The objects are solved by the features of the independent claims. Preferred embodiments are defined in the dependent claims.

According to an independent aspect of the present disclosure, a system for neurological stimulation is provided. The system includes a pulse generator module, a first lead interface module, and a second lead interface module.

Preferably, the pulse generator module includes a first housing configured to accommodate a pulse generator unit, wherein the first housing further includes a coupling portion; and a first electrical interface located at the coupling portion. The pulse generator unit of the pulse generator module may be configured to generate neurological stimulation pulses to be supplied to at least one neurological stimulation electrode via the first electrical interface.

In some embodiments, the first housing may be made of a thermoplastic, such as a PC-ABS alloy.

The at least one neurological stimulation electrode may also be referred to as a "lead". The first lead interface module and the second lead interface module can both be referred to as "external lead adapter".

Preferably, the first lead interface module is connectable to the coupling portion and the first electrical interface of the pulse generator module.

Preferably, the first lead interface module may be detachably connectable to the at least one neurological stimulation electrode. In particular, the first lead interface module may be directly or indirectly connectable to the at least one neurological stimulation electrode.

Preferably, the second lead interface module may be connectable to the coupling portion and the first electrical interface.

Preferably, the second lead interface module may include an extension cable connectable or connected to an electrode coupling box for supplying the neurological stimulation pulses generated by the pulse generator unit to the at least one neurological stimulation electrode. The extension cable may be an interoperative test cable.

Only one of the first lead interface module and the second lead interface module can be connected to the pulse generator module at the same time. In other words, the first lead interface module and the second lead interface module are connectable to the same coupling portion and the same first electrical interface and thus, the first lead interface module and the second lead interface module are not simultaneously connectable to the pulse generator module.

According to a preferred embodiment, the first lead interface module is not connectable to the second lead interface module and vice versa. "Connectable" is understood as e.g. electrically couplable in a manner that electrical signals may be effectively transmitted from the first lead interface module to the second lead interface module and vice versa. If the first and second lead interface module are not connectable to each other, the number of series inter-connections for the inventive system is reduced, thus improving the reliability of the electrical connections, and reduces the overall design complexity, size and weight of the first lead interface module and second lead interface module. Moreover, intraoperative handling of said first and second lead interface module is facilitated for a user by reducing the number of connections.

In some embodiments, the first lead interface module may be connectable to the at least one neurological stimulation electrode during patient worn trialing to supply the neurological stimulation pulses to the at least one neurological stimulation electrode. Additionally, or alternatively, the second lead interface module may be connectable to the at least one neurological stimulation electrode during interoperative testing to supply the neurological stimulation pulses to the at least one neurological stimulation electrode. Accordingly, the system of the present disclosure may support two purposes: intraoperative testing (e.g. for both temporary and permanent leads) and patient-worn trialing.

According to some embodiments, which can be combined with other embodiments described herein, the first lead interface module and/or the second lead interface module includes at least one first connection means attachable to at least one second connection means of the coupling portion. The at least one first connection means and the at least one second connection means may be configured to engage with each other to mechanically connect the respective lead interface module with the pulse generator module.

For example, the at least one first connection means may include at least one protrusion and the at least one second connection means may include at least one recess (e.g. an opening or hole). Alternatively, the at least one first connection means may include at least one recess (e.g. an opening or hole) and the at least one second connection means may include at least one protrusion.

Preferably, the at least one first connection means and the at least one second connection means may provide a rotational axis for the respective lead interface module so that the lead interface module is connectable to the coupling portion by means of a rotation of the lead interface module around the rotational axis. In particular, the at least one first connection means and the at least one second connection means may engage with each other while the lead interface module is tilted with respect to the pulse generator module, and the lead interface module may then be rotated around the rotational axis to align the lead interface module and the pulse generator module. For example, the lead interface module may be rotated to fit or insert the lead interface module into the coupling portion.

Preferably, the pulse generator module and/or the first lead interface module and/or the second lead interface module may include one or more clamps and/or one or more hinge elements configured to fix the lead interface module to the pulse generator module. For example, the one or more clamps and/or the one or more hinge elements may be rotatable around a rotational axis to interlock the lead interface module and the pulse generator module.

According to some embodiments, which can be combined with other embodiments described herein, the coupling portion has a shape essentially corresponding to an outer shape of the first lead interface module and/or the second lead interface module. Accordingly, the coupling portion may accommodate an outer shape of the first lead interface module and/or the second lead interface module.

Preferably, the coupling portion is formed as a cavity or recess on the first housing.

According to some embodiments, which can be combined with other embodiments described herein, the first lead interface module and/or the second lead interface module may include a second electrical interface electrically connectable to the first electrical interface. The second electrical interface may be configured to receive the neurological stimulation pulses generated by the pulse generator unit and supplied via the first electrical interface.

Preferably, the first lead interface module and/or the second lead interface module includes a second housing.

In some embodiments, the second housing may be made of a thermoplastic, such as a PC-ABS alloy.

Preferably, the second housing may have an interior space.

In some embodiments, a first portion of the second electrical interface is arranged at an outside of the second housing and a second portion of the second electrical interface is arranged in the interior space. The first portion may be configured to be electrically connected to the first electrical interface and the second portion may be configured to be (directly or indirectly) electrically connected to the at least one neurological stimulation electrode.

Preferably, the lead interface module, in particular the first lead interface module and not the second lead interface module, includes a lid configured to open or close the interior space of the second housing. In some embodiments, the lid may be rotatably connected to the second housing.

In some embodiments, the lid may be made of a thermoplastic, such as a PC-ABS alloy. Additionally, or alternatively, the lid may be made of a transparent, semi-transparent or opaque material.

According to some embodiments, which can be combined with other embodiments described herein, the first lead interface module and/or the second lead interface module includes a circuit board.

Preferably, the first portion of the second electrical interface is arranged at a first side of the circuit board and the second portion of the second electrical interface is arranged at a second side of the circuit board opposite the first side.

According to some embodiments, which can be combined with other embodiments described herein, the first electrical interface of the pulse generator module includes a plurality of pins, such as pogo pins.

Preferably, the first portion of the second electrical interface includes a plurality of recesses or a plurality of pads configured to engage with the plurality of pins of the first electrical interface when the lead interface module is connected to the coupling portion.

Preferably, the second portion of the second electrical interface includes a plurality of connection elements directly or indirectly connectable to the at least one neurological stimulation electrode.

Preferably, the plurality of connection elements, in particular of the first lead interface module and not the second lead interface module, are arranged to define at least one channel. Each channel may be configured to receive a conductive device or a conductive element. The conductive device may be a part of, or connected to, the at least one neurological stimulation electrode. In some embodiments, the conductive device may be an end portion of the at least one neurological stimulation electrode and may have a plurality of ring contacts.

Preferably, the plurality of connection elements may be configured to radially surround the conductive device. For example, the connection elements may be configured to contact corresponding ring contacts of the conductive device.

Preferably, each connection element of the plurality of connection elements is an essentially U-shaped element having an open top portion. The open top portion may be configured to allow an entry of the conductive device into an inside of the U-shape, in particular in a direction essentially perpendicular to a length extension of the conductive device.

Preferably, the U-shape of the connection element is such that the conductive device is held in the inside of the U-shape after the conductive device has been inserted.

Preferably, each connection element of the plurality of connection elements is formed by a piece of bent metal. The metal may be copper, beryllium copper, or gold. The metal may be also a stable material like beryllium copper with a gold coating or a passivation layer like gold.

Preferably, the plurality of connection elements includes at least one electrical connection element configured to provide the electrical connection to the at least one neurological stimulation electrode and at least one anchor element electrically isolated from the at least one neurological stimulation electrode. The at least one anchor element may be used to grip a non-electrical contact on the at least one neurological stimulation electrode and provide enhanced retention force.

Preferably, a configuration of the at least one electrical connection element and a configuration of the at least one anchor element are essentially identical.

Preferably, the plurality of connection elements are soldered to a circuit board of the lead interface module, in particular the first lead interface module.

Preferably, the plurality of connection elements are manufactured as a gang (e.g. 8 electrical contacts and 1 anchor contact) and then electrically isolated; this helps ensure uniformity in the dimensions of the connection elements.

According to some embodiments, which can be combined with other embodiments described herein, the plurality of connection elements of the second lead interface module are solder pads. The extension cable may be soldered to the solder pads. Accordingly, unlike the first lead interface module, the extension cable is fixedly connected to the second lead interface module and is not detachable.

According to some embodiments, which can be combined with other embodiments described herein, the system further includes the electrode coupling box. The electrode coupling box may be connectable or connected to the at least one neurological stimulation electrode. The electrode coupling box may be configured to electrically connect the second lead interface module and the at least one neurological stimulation electrode. Thereby, the neurological stimulation pulses generated by the pulse generator unit are transferred to the at least one neurological stimulation electrode via the electrode coupling box.

Preferably, the electrode coupling box may be mechanically connectable to the at least one neurological stimulation electrode. For example, the electrode coupling box may be detachably connectable to the at least one neurological stimulation electrode.

Preferably, the extension cable has a first end portion fixedly connected to the second lead interface module and a second end portion connected to the electrode coupling box.

Preferably, the electrode coupling box may be configured to electrically connect the second end portion of the extension cable and the at least one neurological stimulation electrode such that the neurological stimulation pulses generated by the pulse generator unit are transferred to the at least one neurological stimulation electrode via the second lead interface module, the extension cable, and the electrode coupling box.

According to another independent aspect of the present disclosure, which can be combined with the other aspects described herein, a system for neurological stimulation is provided.

The system includes a pulse generator module and a lead interface module. The pulse generator module includes a first housing configured to accommodate a pulse generator unit, wherein the first housing includes a coupling portion; and a first electrical interface located at the coupling portion. The lead interface module is connectable to the coupling portion and at least one neurological stimulation electrode, wherein the lead interface module includes a second electrical interface connectable to the first electrical interface when the lead interface module is connected to the coupling portion, for supplying neurological stimulation pulses generated by the pulse generator unit to the at least one neurological stimulation electrode.

According to another independent aspect of the present disclosure, which can be combined with the other aspects described herein, a system for neurological stimulation is provided. The system includes a pulse generator module having a first electrical interface, wherein the pulse generator module is configured to supply neurological stimulation pulses to at least one neurological stimulation electrode via the first electrical interface; a first lead interface module detachably connectable to the first electrical interface of the pulse generator module, wherein the first lead interface module is connectable to the at least one neurological stimulation electrode during patient worn trialing to supply the neurological stimulation pulses to the at least one neurological stimulation electrode; and a second lead interface module detachably connectable to the first electrical interface of the pulse generator module, wherein the second lead interface module is connectable to the at least one neurological stimulation electrode during interoperative testing to supply the neurological stimulation pulses to the at least one neurological stimulation electrode.

According to another independent aspect of the present disclosure, which can be combined with the other aspects described herein, a pulse generator module for neurological stimulation is provided. The pulse generator module includes a first housing having a coupling portion, wherein the coupling portion is releasably mechanically connectable to (one of) a first lead interface module and a second lead interface module different from the first lead interface module.

The pulse generator module may further include a first electrical interface located at the coupling portion, wherein the first electrical interface is arranged to be electrically connected to a second electrical interface of the first lead interface module when the first lead interface module is connected to the coupling portion, and another second electrical interface of the second lead interface module when the second lead interface module is connected to the coupling portion.

The first lead interface module may be connectable to the at last one neurological stimulation electrode during patient worn trialing to supply the pulses to the at last one neurological stimulation electrode. Additionally, or alternatively, the second lead interface module may be connectable to the at least one neurological stimulation electrode during interoperative testing to supply the pulses to the at last one neurological stimulation electrode.

According to another independent aspect of the present disclosure, which can be combined with the other aspects described herein, a lead interface module is provided. The lead interface module is detachably connectable to a pulse generator module, wherein the lead interface module is further connectable to at least one neurological stimulation electrode during patient worn trialing to supply neurological stimulation pulses generated by the pulse generator module to the at least one neurological stimulation electrode.

Preferably, the lead interface module is directly connectable to the at least one neurological stimulation electrode.

According to another independent aspect of the present disclosure, which can be combined with the other aspects described herein, a lead interface module is provided. The lead interface module is detachably connectable to a pulse generator module, wherein the lead interface module is connectable to at least one neurological stimulation electrode during interoperative testing to supply neurological stimulation pulses generated by the pulse generator module to the at least one neurological stimulation electrode.

Preferably, the lead interface module is connectable to the at least one neurological stimulation electrode via an extension cable and/or an electrode coupling box.

So that the manner in which the above recited features of the present disclosure can be understood in detail, a more particular description of the disclosure, briefly summarized above, may be had by reference to embodiments. The accompanying drawings relate to embodiments of the disclosure and are described in the following:

Reference will now be made in detail to the various embodiments of the disclosure, one or more examples of which are illustrated in the figures. Within the following description of the drawings, the same reference numbers refer to same components. Generally, only the differences with respect to individual embodiments are described. Each example is provided by way of explanation of the disclosure and is not meant as a limitation of the disclosure. Further, features illustrated or described as part of one embodiment can be used on or in conjunction with other embodiments to yield yet a further embodiment. It is intended that the description includes such modifications and variations.

Spinal cord stimulation therapies are not effective for all patients. Prior to receiving a permanent implant, it is common practice to utilize a screening approach to evaluate which patients respond to therapy. The screening consists of two phases: intraoperative testing and patient-worn trialing.

The present disclosure provides a system which includes a reusable external pulse generator that supports multiple modes of use, namely intraoperative testing and patient-worn trialing. In particular, the same external pulse generator is connectable to two different lead interface modules, one of which can be used during intraoperative testing and another one which can be used during patient-worn trialing. This can reduce the cost of spinal cord stimulation therapies. Further benefits of the present disclosure are apparent from the following description and the accompanying drawings.

Figure 1:
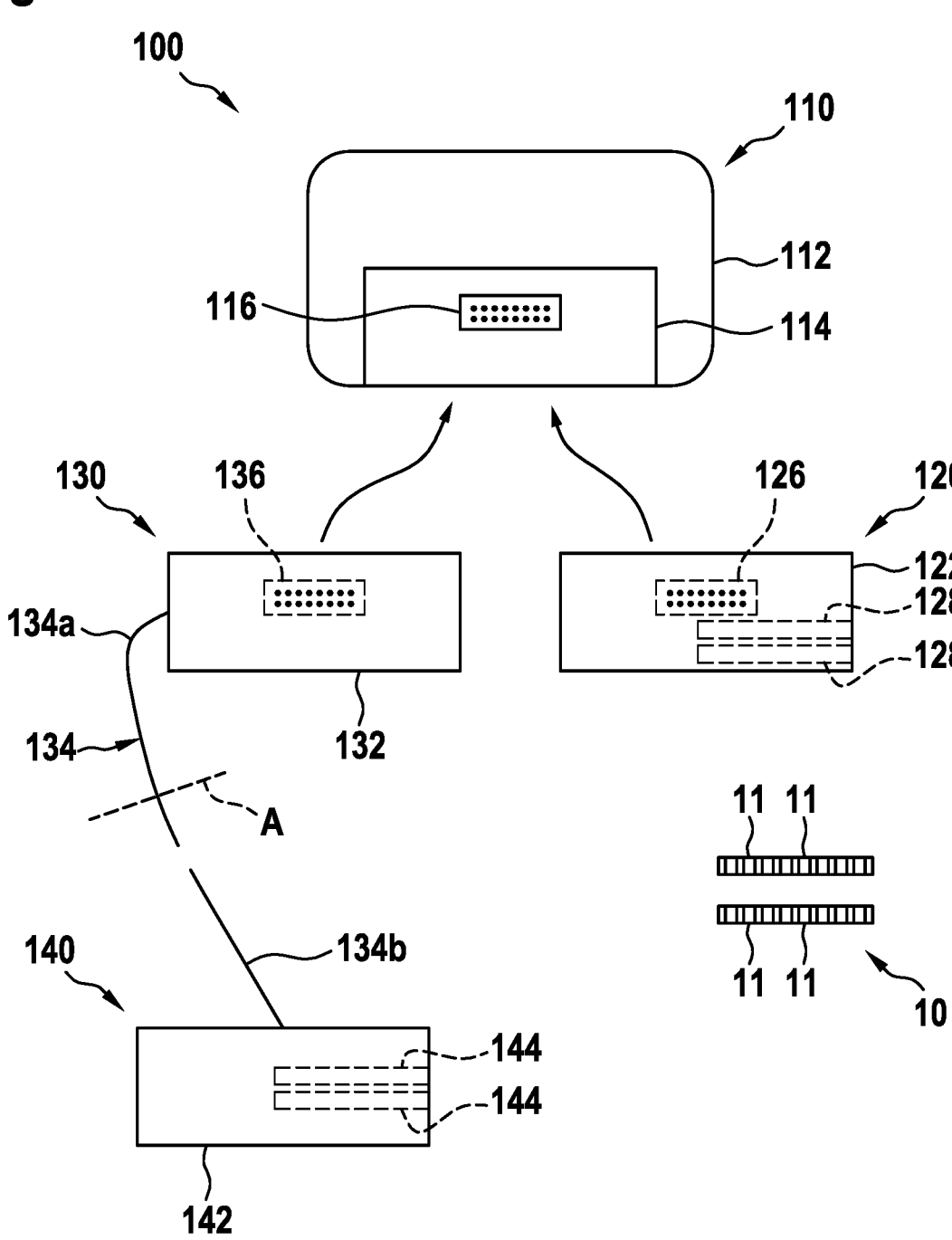
FIG. 1 shows a schematic view of a system for neurological stimulation according to embodiments of the present disclosure.

FIG. 1 shows a schematic view of a system 100 for neurological stimulation according to embodiments of the present disclosure.

The system 100 includes a pulse generator module 110, a first lead interface module 120, and a second lead interface module 130. The pulse generator module 110 may also be referred to as "external pulse generator" (EPG).

Either the first lead interface module 120 or the second lead interface module 130 may be connected to the pulse generator module 110. In other words, the first lead interface module 120 and the second lead interface module 130 are connectable to the same coupling portion 114 and the same first electrical interface 116 and thus, the first lead interface module 120 and the second lead interface module 130 are not simultaneously connectable to the pulse generator module 110.

The pulse generator module 110 may include a first housing 112 configured to accommodate a pulse generator unit (not shown). The pulse generator unit may be configured to generate neurological stimulation pulses to be supplied to at least one neurological stimulation electrode 10. The at least one neurological stimulation electrode 10 may also be referred to as a "lead".

The at least one neurological stimulation electrode 10 may include a portion that is placed percutaneously within the patient's body to deliver the neurological stimulation pulses to the spinal cord. The neurological stimulation electrode 10 may further have another portion outside the patient's body and which is connectable to the pulse generator module 110 via the first lead interface module 120 or the second lead interface module 130. In particular, the first lead interface module 120 and the second lead interface module 130 may adapt the at least one neurological stimulation electrode 10, such as one or more percutaneous leads, to the pulse generator module 110.

For example, the at least one neurological stimulation electrode 10 may have an end portion which has a plurality of ring contacts 11 used to electrically connect the at least one neurological stimulation electrode 10 to the first lead interface module 120 and/or the second lead interface module 130. The basic design of neurological stimulation electrodes is known in the art and is therefore not explained in detail.

The pulse generator module 110 supports the two detachable lead interface modules 120, 130 with a common electrical and mechanical interface. For this purpose, the first housing 112 includes a coupling portion 114 and a first electrical interface 116. The first electrical interface 116 is located at, or in, the coupling portion 114. The neurological stimulation pulses generated by the pulse generator unit are supplied to the to at least one neurological stimulation electrode 10 via the first electrical interface 116.

Expressions such as "detachably connected" and "releasably connected" are used to distinguish from "permanently connected" and "fixedly connected".

The first lead interface module 120 is connectable, in particular detachably connectable, to the coupling portion 114 and the first electrical interface 116 of the pulse generator module 110. In particular, the first lead interface module 120 may be mechanically connectable to the coupling portion 114 and electrically connectable to the first electrical interface 116.

The first lead interface module 120 may include a second electrical interface 126 electrically connectable to the first electrical interface 116, for example, by means of a mechanical contact between the first electrical interface 116 and the second electrical interface 126. The second electrical interface 126 may be configured to receive the neurological stimulation pulses generated by the pulse generator unit and supplied via the first electrical interface 116.

Preferably, the first lead interface module 120 includes a second housing 122. The second electrical interface 126 may be exposed from the second housing 122 e.g. via openings in the second housing 122 to allow a mechanical and therefore electrical contact between the first electrical interface 116 and the second electrical interface 126 when the first lead interface module 120 is mounted at the coupling portion 114.

In some embodiments, the first lead interface module 120 may be detachably connectable to the at least one neurological stimulation electrode 10. In particular, the first lead interface module 120 may be directly or indirectly connectable to the at least one neurological stimulation electrode 10.

The direct connection means that the at least one neurological stimulation electrode 10 is connected to the first lead interface module 120 without intermediate means, such as cables or devices. For example, the second housing 122 of the first lead interface module 120 may have one or more openings 128 to allow an entry of the at least one neurological stimulation electrode 10. In particular, an end portion of the at least one neurological stimulation electrode 10 may be insertable into the first lead interface module 120 via the one or more openings 128 to establish an electrical connection between the at least one neurological stimulation electrode 10 and the second electrical interface 126.

The indirect connection means that the at least one neurological stimulation electrode 10 is connected to the first lead interface module 120 via one or more intermediate means, such as cables and/or devices. In this case, the intermediate means may be insertable into the first lead interface module 120 via the one or more openings 128 to establish an electrical connection between the intermediate means (and therefore the at least one neurological stimulation electrode 10) and the second electrical interface 126.

In some embodiments, the first lead interface module 120 is connected to the at least one neurological stimulation electrode 10 during patient worn trialing to supply the neurological stimulation pulses generated by the pulse generator module 110 to the at least one neurological stimulation electrode 10.

The second lead interface module 130 is connectable, in particular detachably connectable, to the coupling portion 114 and the first electrical interface 116 of the pulse generator module 110. In particular, the second lead interface module 130 may be mechanically connectable to the coupling portion 114 and electrically connectable to the first electrical interface 116.

The second lead interface module 130 may include another second electrical interface 136 electrically connectable to the first electrical interface 116, for example, by means of a mechanical contact between the first electrical interface 116 and the other second electrical interface 136. The other second electrical interface 136 may be configured to receive the neurological stimulation pulses generated by the pulse generator unit and supplied via the first electrical interface 116.

Preferably, the second lead interface module 130 includes another second housing 132. The other second electrical interface 136 may be exposed from the other second housing 132 e.g. via one or more openings in the other second housing 132 to allow a mechanical and therefore electrical contact between the first electrical interface 116 and the other second electrical interface 136 when the second lead interface module 130 is mounted at the coupling portion 114.

The system 100, in particular the second lead interface module 130, may include an extension cable 134 connectable or connected to an electrode coupling box 140 for supplying the neurological stimulation pulses generated by the pulse generator unit to the at least one neurological stimulation electrode 10.

The extension cable 134 may have a first end portion 134*a* fixedly or permanently connected to the second lead interface module 130 and a second end portion 134*b* connected to the electrode coupling box 140. The second end portion 134*b* may be permanently or detachably connected to the electrode coupling box 140.

The electrode coupling box 140 may be electrically connectable or connected to the at least one neurological stimulation electrode 10 to establish an electrical connection between the second lead interface module 130 and the at least one neurological stimulation electrode 10. Thereby, the neurological stimulation pulses generated by the pulse generator unit can be transferred to the at least one neurological stimulation electrode 10 via the electrode coupling box 140.

The at least one neurological stimulation electrode 10 may be permanently or detachably connected to the electrode coupling box 140.

In some embodiments, the electrode coupling box 140 may include a coupling box housing 142. The coupling box housing 142 may have one or more openings 144 to allow an entry of the at least one neurological stimulation electrode 10. In particular, an end portion of the at least one neurological stimulation electrode 10 may be insertable into the electrode coupling box 140 via the one or more openings 144 to establish an electrical connection between the at least one neurological stimulation electrode 10 and the extension cable 134.

In some embodiments, the coupling box housing 142 may be made of a thermoplastic, such as a PC-ABS alloy.

In some embodiments, the second lead interface module 130 may be connectable to the at least one neurological stimulation electrode 10 during interoperative testing to supply the neurological stimulation pulses to the at least one neurological stimulation electrode 10. Due to the extension cable 134, the pulse generator module 110 and the second lead interface module 130 may remain outside of the surgical sterile field and only the electrode coupling box 140 may be located within the surgical sterile field. In FIG. 1 the surgical sterile field is indicated with a dashed line A. Accordingly, at least the pulse generator module 110 is reusable, especially since the electronics of the system 100 are contained therein and remain outside the surgical sterile field.

Figure 2A:
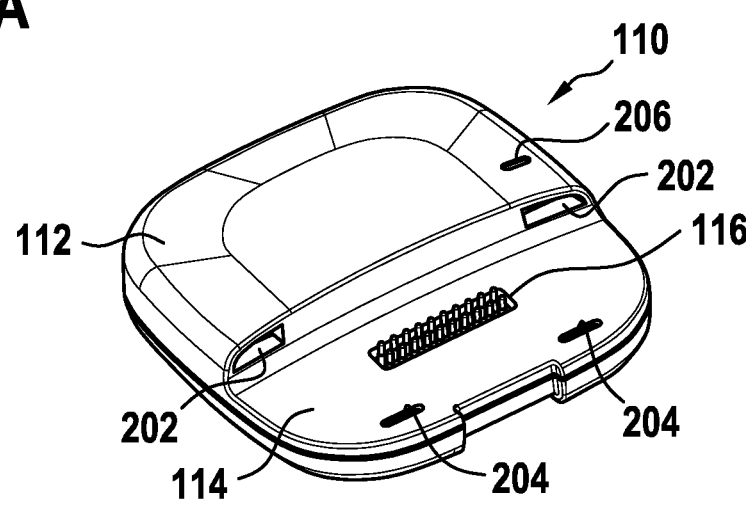
FIGS. 2A and 2B show perspective views of a pulse generator module according to embodiments of the present disclosure.
Figure 2B:
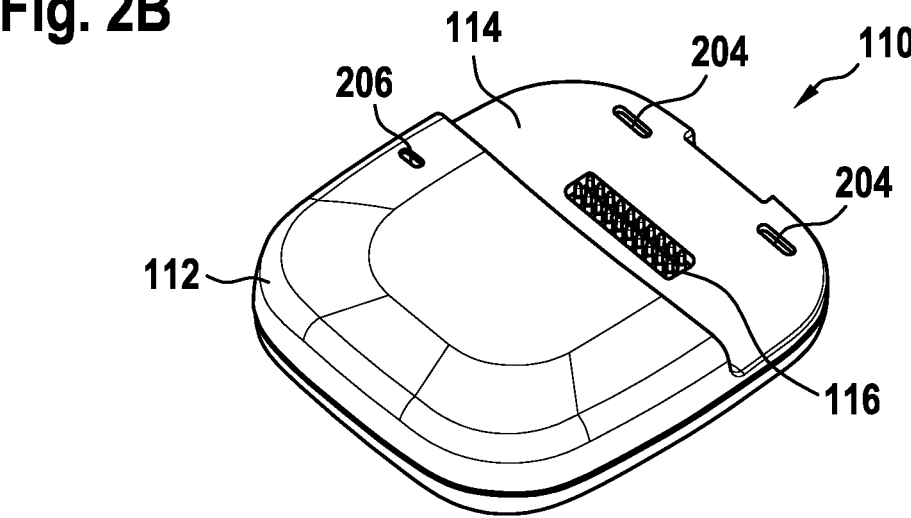
Figure 2C:
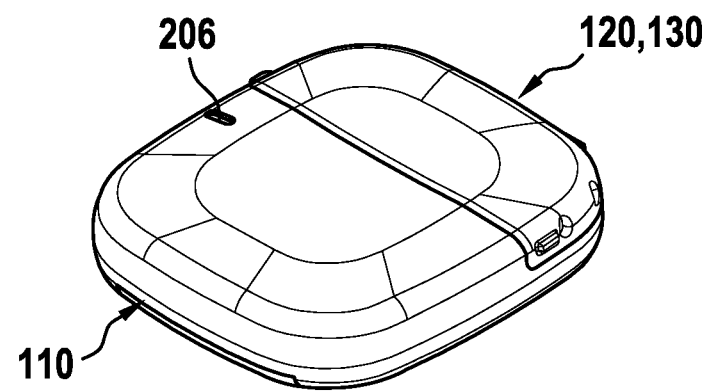
FIG. 2C shows a perspective view of a pulse generator module with mated lead interface module according to embodiments of the present disclosure.

FIGS. 2A and 2B show perspective views of a pulse generator module 110 according to embodiments of the present disclosure. FIG. 2C shows a perspective view of the pulse generator module 110 with mated lead interface module 120 or 130 according to embodiments of the present disclosure.

The first housing 112 of the pulse generator module 110 provides the coupling portion 114, to which the first lead interface module 120 and the second lead interface module 130 are connectable. In some embodiments, the coupling portion 114 is formed as a cavity or recess on the first housing 112. The cavity or recess may be configured to accommodate the first lead interface module 120 and/or the second lead interface module 130, in particular an outer shape thereof.

For example, the coupling portion 114 can have a shape essentially corresponding to an outer shape of the first lead interface module 120 and/or the second lead interface module 130. When the lead interface module is mounted to the coupling portion 114, the outer shape of the lead interface module and the outer shape of the first housing 112 of the pulse generator module 110 may be flush. As is shown in FIG. 2C, this can improve the appearance, as the pulse generator module 110 and the lead interface module connected thereto have a continuous and smooth exterior.

According to some embodiments, which can be combined with other embodiments described herein, the first lead interface module 120 and/or the second lead interface module 130 can include at least one first connection means attachable to at least one second connection means 202 of the coupling portion 114. The at least one first connection means and the at least one second connection means 202 may be configured to engage with each other to mechanically connect the respective lead interface module to the pulse generator module 110. This will be discussed in more detail later with reference to FIGS. 3A and 3B.

According to some embodiments, which can be combined with other embodiments described herein, the pulse generator module 110 can include holding means configured to secure and/or retain the lead interface module once the lead interface module has been mounted to the coupling portion 114. In particular, the holding means may be configured to mechanically retain the lead interface module from lateral and rotational movement once secured.

Figure 14:
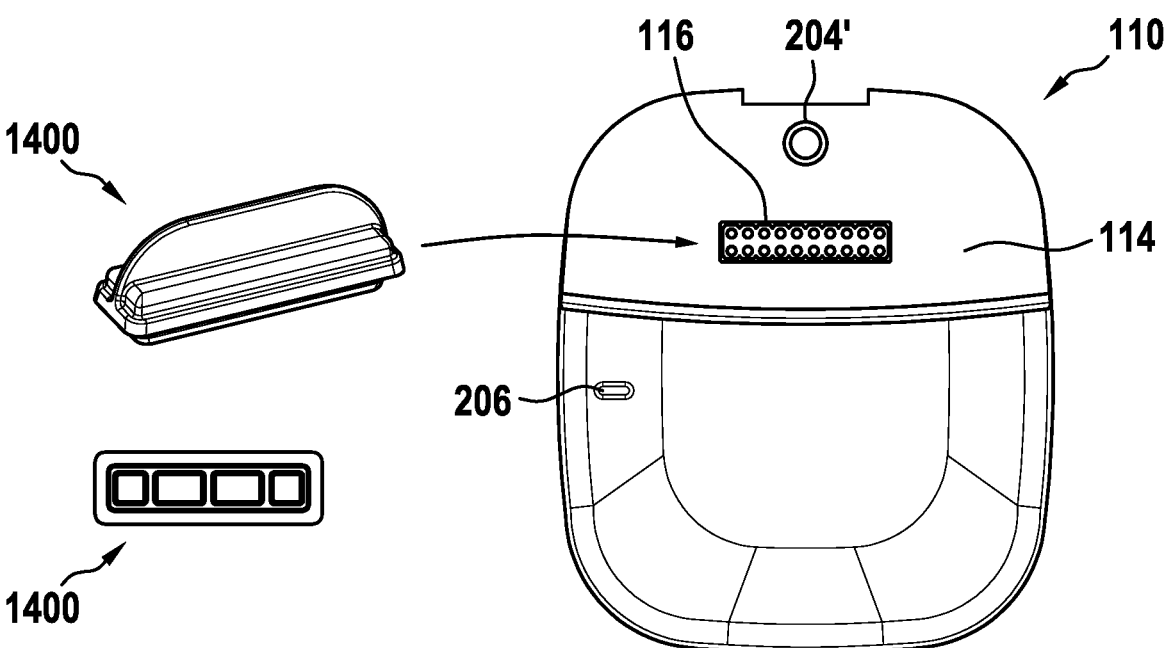
FIG. 14 shows a top view of a pulse generator module and an interface cap according to embodiments of the present disclosure.

For example, the holding means may include at least one holding protrusion and at least one holding recess 204 configured to engage with the at least one holding protrusion. The at least one holding protrusion can be a fin, and the at least one holding recess can be a corresponding cavity. An alternative circular configuration of the holding means is shown in FIG. 14.

In the example of FIGS. 2A and 2B, the at least one holding recess 204 is provided at the first housing 112, particularly the coupling portion 114. Corresponding holding protrusions are provided at the lead interface module (not shown). Alternatively, the at least one holding protrusion is provided at the first housing 112, particularly the coupling portion 114. Corresponding holding recesses can be provided at the lead interface module.

Additionally, or alternatively, the holding means can include one or more clamps and/or one or more hinge elements configured to fix the lead interface module to the pulse generator module 110. The clamps/hinges will be discussed in more detail later with reference to FIGS. 3B and 4.

In some embodiments, the pulse generator module 110 may include at least one indicator 206 configured to indicate an operational state of the system 100, such as ON or OFF. Other operational states can be: Bluetooth pairing mode entry or battery attach feedback. The at least one indicator 206 may be located at the first housing 112. The at least one indicator 206 may be a light source, such as an LED and/or a multi-color light source.

Figure 3A:
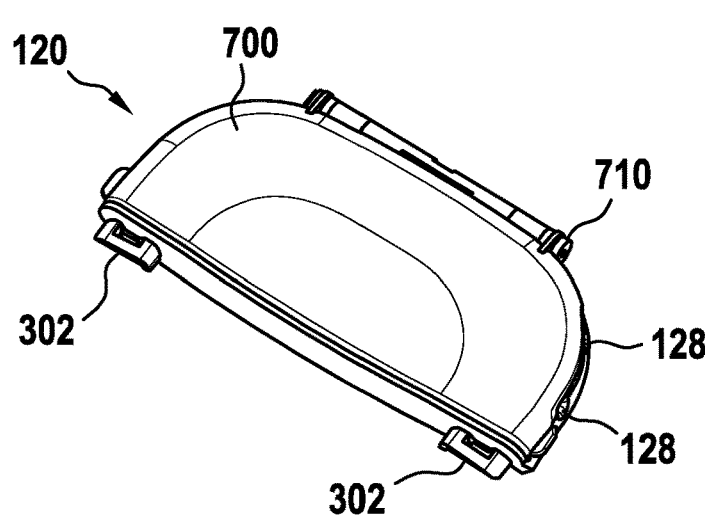
FIGS. 3A, 3B and 3C show perspective views of a first lead interface module according to embodiments of the present disclosure.
Figure 3B:
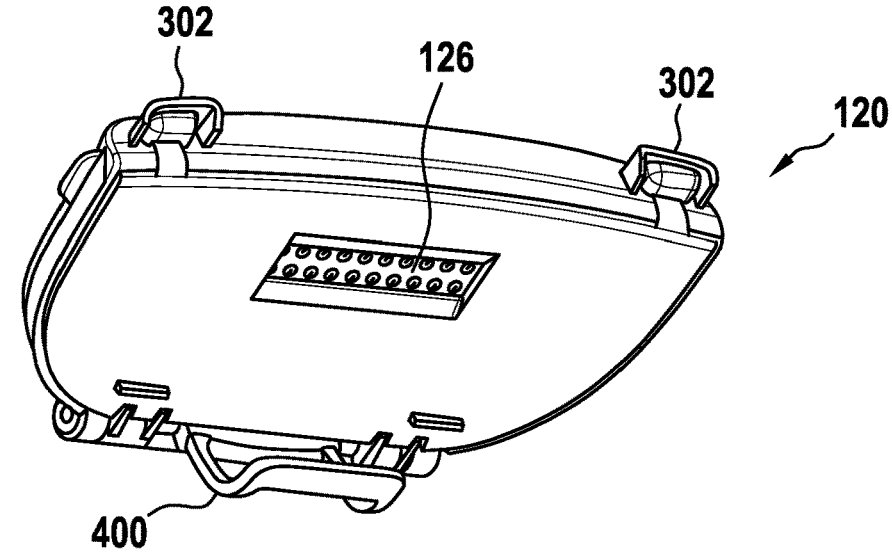
Figure 3C:
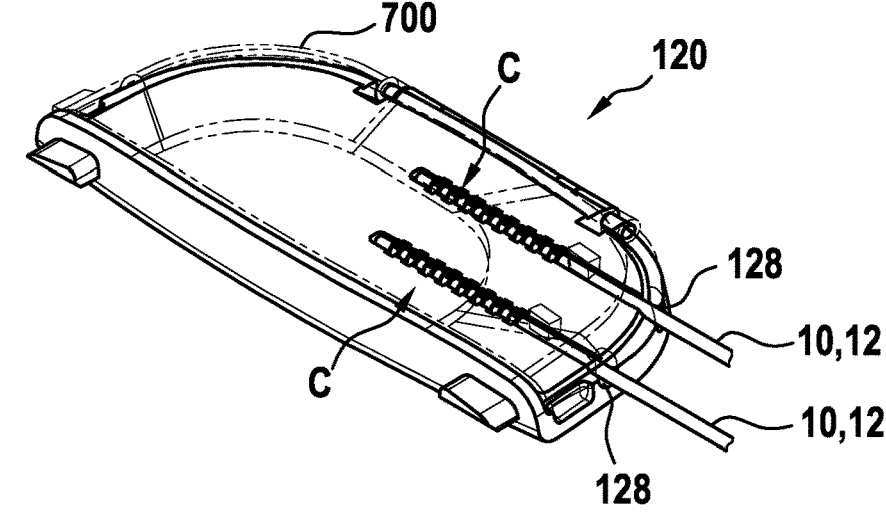
Figure 3D:
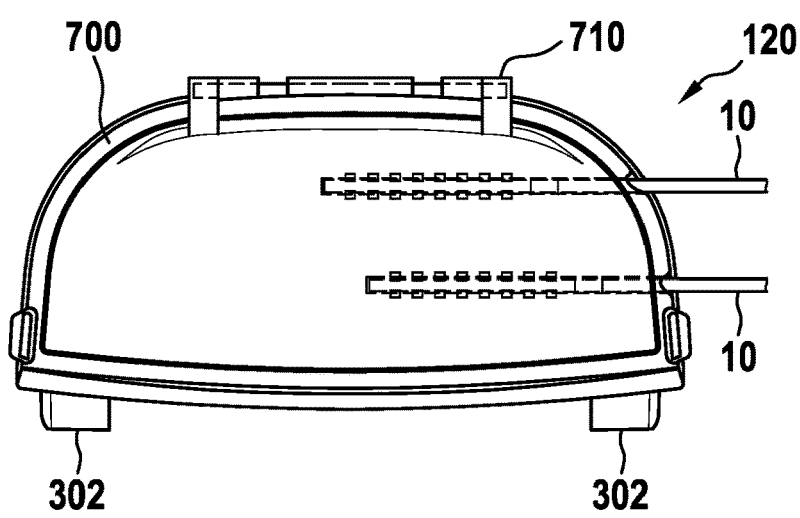
FIG. 3D shows a top view of the first lead interface module.
Figure 3E:
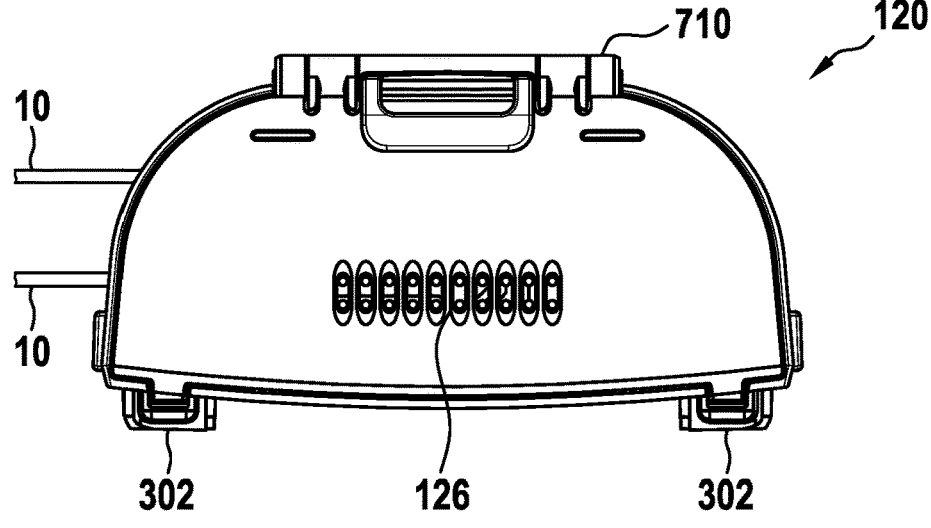
FIG. 3E shows a bottom view of the first lead interface module.
Figure 4:
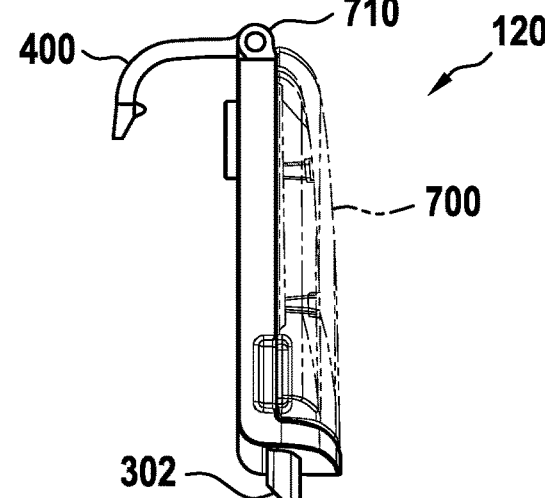
FIG. 4 shows a side view of the first lead interface module.

FIGS. 3A, 3B and 3C show perspective views of a first lead interface module 120 according to embodiments of the present disclosure. FIG. 3D shows a top view of the first lead interface module 120. FIG. 3E shows a bottom view of the first lead interface module 120. FIG. 4 shows a side view of the first lead interface module 120.

According to some embodiments, which can be combined with other embodiments described herein, the first lead interface module 120 includes at least one first connection means 302 attachable to the at least one second connection means 202 of the pulse generator module 110 shown in FIG. 2A. The at least one first connection means 302 and the at least one second connection means 202 may be configured to engage with each other to mechanically connect the first lead interface module 120 and the pulse generator module.

For example, the at least one first connection means 302 includes at least one protrusion and the at least one second connection means 202 includes at least one recess (e.g. an opening or hole). Alternatively, the at least one first connection means includes at least one recess (e.g. an opening or hole) and the at least one second connection means 202 includes at least one protrusion.

Preferably, the at least one first connection means 302 and the at least one second connection means 202 provide a rotational axis for the first lead interface module 120 so that the first lead interface module 120 is connectable to the coupling portion by means of a rotation of the first lead interface module 120 around the rotational axis. In particular, the at least one first connection means 302 and the at least one second connection means 202 may engage with each other while the first lead interface module 120 is tilted with respect to the pulse generator module, and the first lead interface module 120 may then be rotated downwards around the rotational axis to align the first lead interface module 120 and the pulse generator module. For example, the first lead interface module 120 may be rotated to fit or insert the first lead interface module 120 into the coupling portion, as it is shown in FIG. 2C.

Preferably, the first lead interface module 120 includes the second housing 122. The second housing 122 may have an interior space and a lid 700 configured to open or close the interior space of the second housing 122. For example, the second housing 122 may define the interior space and may have an open top portion covered by the lid 700.

In some embodiments, the lid 700 may be rotatably connected to the second housing 122 by means of a rotational axis 710. The rotational axis 710 may be provided at a side of the interior space opposite to a side at which the at least one first connection means 302 is located. In other words, the interior space may be located between the at least one first connection means 302 and the rotational axis 710. Therefore, the lid 700 can be opened by rotating it outward.

In some embodiments, the second housing 122 of the first lead interface module 120 may have one or more openings 128 to allow an entry of the at least one neurological stimulation electrode 10. In particular, an end portion 12 of the at least one neurological stimulation electrode 10 may be insertable into the first lead interface module 120, in particular the interior space, via the one or more openings 128 to establish an electrical connection between the at least one neurological stimulation electrode 10 and the second electrical interface 126.

For example, the end portion 12 of the at least one neurological stimulation electrode 10 may have plurality of ring contacts 11 used to electrically connect the at least one neurological stimulation electrode 10 to the first lead interface module 120.

In some implementation, the electrical connection between the at least one neurological stimulation electrode 10 and the second electrical interface 126 can be established by means of a conductive channel C into which the at least one neurological stimulation electrode 10 or the end portion 12 thereof is insertable. The content of the interior space, in particular the conductive channel C, will be discussed in more detail later with reference to FIGS. 4B and 5B.

In some implementations, the first lead interface module 120 includes one or more clamps and/or one or more hinge elements 400 configured to fix the first lead interface module 120 to the pulse generator module. For example, the one or more clamps and/or the one or more hinge elements 400 may be rotatable around a rotational axis to interlock the first lead interface module 120 and the pulse generator module. In particular, a rotating hinge may be provided which snaps into place on the pulse generator module when the first lead interface module 120 is fully seated in the coupling portion of the pulse generator module.

In some embodiments, the rotating axis of the one or more clamps and/or one or more hinge elements 400 and the rotating axis 710 of the lid may be the same rotating axis.

The second lead interface module can be configured similar to the first lead interface module and a description of similar or identical aspects is omitted. In particular, the second lead interface module can include the holding means and/or the second housing and/or the at least one first connection means and/or the one or more clamps/hinges and/or the lid.

Figure 5A:
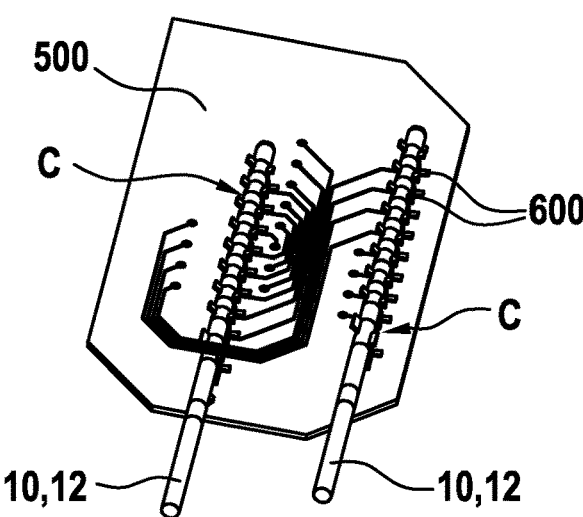
FIG. 5A shows a perspective view of a circuit board of the first lead interface module.
Figure 5B:
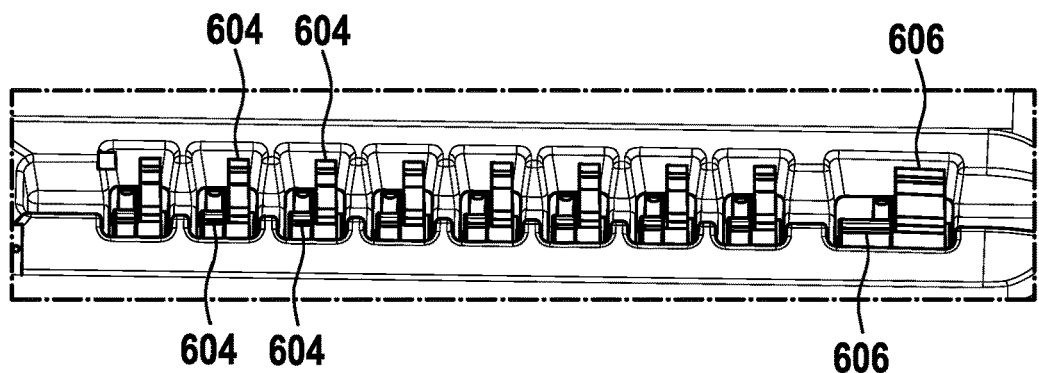
FIG. 5B shows a schematic view of a conductive channel for connecting a neurological stimulation electrode to the first lead interface module.

FIG. 5A shows a perspective view of a circuit board 500 of the first lead interface module. FIG. 5B shows a schematic view of conductive channels C for connecting a neurological stimulation electrode to the first lead interface module.

The circuit board 500 may be arranged in the interior space of the second housing and may be connected to, or part of, the second electrical interface of the first lead interface module which is connectable to the first electrical interface of the pulse generator module.

The circuit board 500 may have a first side and a second side opposite the first side. The first side may face a bottom of the second housing, and the second side may face the open top portion of the interior space, in particular the lid.

Different portions of the second electrical interface can be located on the first side and the second side of the circuit board 500, and some parts of the second electrical interface can penetrate the circuit board 500 to connect the different portions of the second electrical interface.

In some embodiments, a first portion of the second electrical interface is exposed to an outside of the second housing e.g. via one or more openings in the second housing, and a second portion of the second electrical interface is arranged in the interior space. The first portion may be configured to be electrically connected to the first electrical interface and the second portion may be configured to be (directly or indirectly) electrically connected to the at least one neurological stimulation electrode 10 or the end portion 12 thereof which has the plurality of ring contacts.

Preferably, the first portion of the second electrical interface is arranged at the first side of the circuit board 500 and the second portion of the second electrical interface is arranged at the second side of the circuit board 500 opposite the first side.

In order to electrically connect the second electrical interface to the first electrical interface of the pulse generator module, the first electrical interface of the pulse generator module may include a plurality of pins, such as an array of pins and/or pogo pins. The first portion of the second electrical interface may include a plurality of recesses or a plurality of pads, such as copper pads, configured to engage with the plurality of pins of the first electrical interface when the lead interface module is connected to the coupling portion. The pins will be discussed in more detail later with reference to FIGS. 11 and 12.

The second portion of the second electrical interface, which is located at the second side of the circuit board, may include a plurality of connection elements 600 directly connectable to the at least one neurological stimulation electrode 10 or the end portion 12 thereof. The plurality of connection elements 600 can be soldered to the circuit board 500, in particular the second side of the circuit board 500. The plurality of connection elements 600 can be electrically connected to the first portion of the second electrical interface, such as the plurality of recesses or plurality of pads which are configured to engage with the plurality of pins of the first electrical interface.

Preferably, the plurality of connection elements 600 are arranged to define at least one conductive channel C. Each channel C may be configured to receive a conductive device of the at least one neurological stimulation electrode 10 or connected to the at least one neurological stimulation electrode 10. In some embodiments, the conductive device may be an external part of the at least one neurological stimulation electrode 10, such as the end portion 12 of the at least one neurological stimulation electrode 10.

Preferably, the plurality of connection elements 600 are configured to radially surround the conductive device, such as the end portion 12 or the ring contacts of the end portion 12.

In the example of FIGS. 5A and 5B, two conductive channels and two neurological stimulation electrodes 10 respectively connected to the conductive channels are shown. However, the present disclosure is not limited thereto, and one conductive channel and one corresponding neurological stimulation electrode can be provided, or three or more conductive channels and three or more corresponding neurological stimulation electrodes can be provided.

Referring to FIG. 5B, the plurality of connection elements 600 may include at least one electrical connection element 604 configured to provide the electrical connection to the at least one neurological stimulation electrode 10 (e.g. the ring contacts of the end portion 12) and at least one anchor element 606 electrically isolated from the at least one neurological stimulation electrode 10. The at least one anchor element 606 may be used to grip a non-electrical contact on the at least one neurological stimulation electrode 10 and provide enhanced retention force.

Preferably, a configuration of the at least one electrical connection element 604 and a configuration of the at least one anchor element 606 are essentially identical. The expression "essentially identical" means that shape and/or cross-sections of the elements are the same. However, a length of the elements may be different. For example, a length of the at least one anchor element 606 in a length direction of the conductive channel C may be larger than a length of the at least one electrical connection element 604 in the length direction of the conductive channel C.

In some embodiments, the plurality of connection elements 600 can be manufactured as at least one gang (e.g. 8 electrical contacts and 1 anchor contact per conductive channel or 8-pol percutaneous lead) and then electrically isolated; this helps ensure uniformity in the dimensions of the connection elements.

Figure 6:
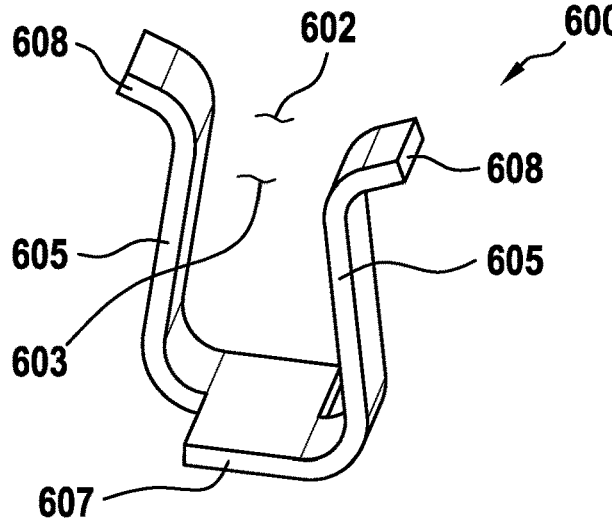
FIG. 6 shows a perspective view of a connection element used to form the conductive channel.

FIG. 6 shows a perspective view of a connection element 600 used to form the conductive channel.

In some embodiments, the connection element 600 is an essentially U-shaped element having an open top portion 602. The open top portion 602 may be configured to allow an entry of the conductive device, such as the end portion 12 of the neurological stimulation electrode 10, into an inside or cavity 603 of the U-shape. For example, the open top portion 602 may be configured to allow an entry of the conductive device into the inside or cavity 603 of the U-shape in a direction essentially perpendicular to a length extension of the conductive channel and/or the conductive device 600.

Preferably, the U-shape of the connection element 600 is such that the conductive device is held in the inside of the U-shape after the conductive device has been inserted. For example, the U-shape may have inwardly bent legs 605 which are pushed in opposite directions to enlarge the open top portion 602 when the conductive device is inserted. An elasticity of the material of the connection element 600 may provide a restoring force which attempts to move the outwardly bent legs 605 inwards to their initial or neutral position, thereby providing a clamping force holding the conductive device inside the U-shape.

Accordingly, the connection element 600 deforms outwardly to receive the conductive device, such as the end portion of the neurological stimulation electrode, and its ring contacts, hold it in place and make electrical contact. The conductive device may be flush or sub flush in all connection elements 600 when fully inserted.

The connection element 600 may include a smooth guiding portion which directs the (e.g. circular) conductive device e.g. with ring contacts into the inside of the connection element 600 where the conductive device is retained when the conductive device is pressed into an array of connection elements 600. For example, the bent legs 605 may have outwardly bent edges 608 at the open top portion 602 to facilitate the guiding of the conductive device.

In some embodiments, the connection element 600 can include a solderable surface 607 to adhere to the circuit board of the first lead interface module e.g. using surface mount soldering technology. The solderable surface 607 may be an essentially flat surface and/or can be located at a side of the connection element 600 opposite the open top portion 602.

Preferably, the connection elements are soldered down as a gang and subsequently electrically isolated by cutting them apart.

Preferably, the connection element 600 is formed by a piece of bent metal. Additionally, or alternative, the metal may be copper, beryllium copper, or gold.

Figure 7A:
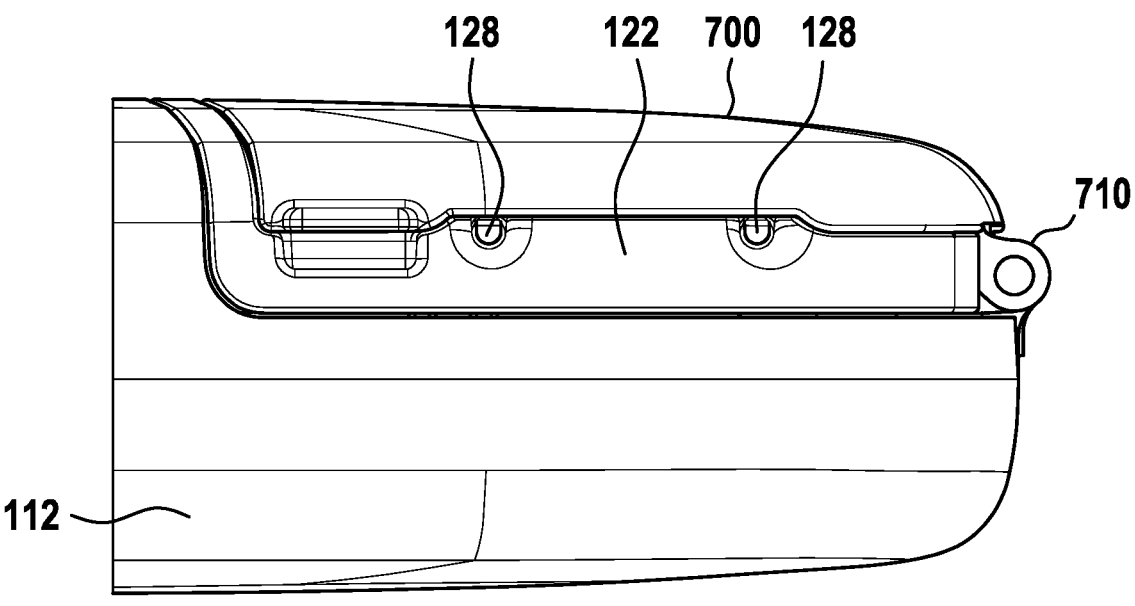
FIG. 7A shows a side view of a pulse generator module with mated first lead interface module according to embodiments of the present disclosure.
Figure 7B:
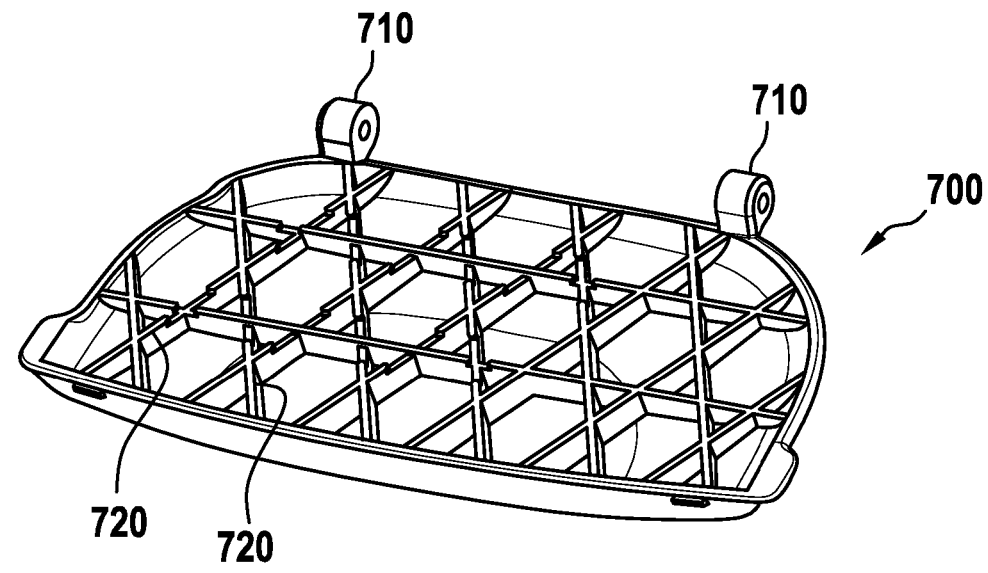
FIG. 7B shows a perspective view of a lid of the lead interface module according to embodiments of the present disclosure.

FIG. 7A shows a side view of a pulse generator module with mated first lead interface module according to embodiments of the present disclosure. FIG. 7B shows a perspective view of a lid 700 of the lead interface module according to embodiments of the present disclosure.

The lid 700 may be configured to open or close the interior space of the second housing 122 of the first lead interface module. In some embodiments, the lid 700 may be rotatably connected to the second housing 122 by means of a rotational axis 710. The lid 700 can be opened by rotating it outward.

The lid 700 can include one or more ribs 720 to enhance a rigidity of the lid 700. In some embodiments, the one or more ribs 720 do not contact the portion of the neurological stimulation electrode(s) located in the second housing 122.

According to some embodiments, which can be combined with other embodiments described herein, the lid 700 may be made of a transparent or semi-transparent material. For example, the lid 700 may be made of plastic, such as an opaque plastic.

Although the lid 700 has been described with reference to the first lead interface module, it is to be understood that the second lead interface module may have a similar or identical lid. However, in other embodiments, the second lead interface module may not a lid which can be opened. In particular, the second lead interface module may not have a lid at all.

Figure 8:
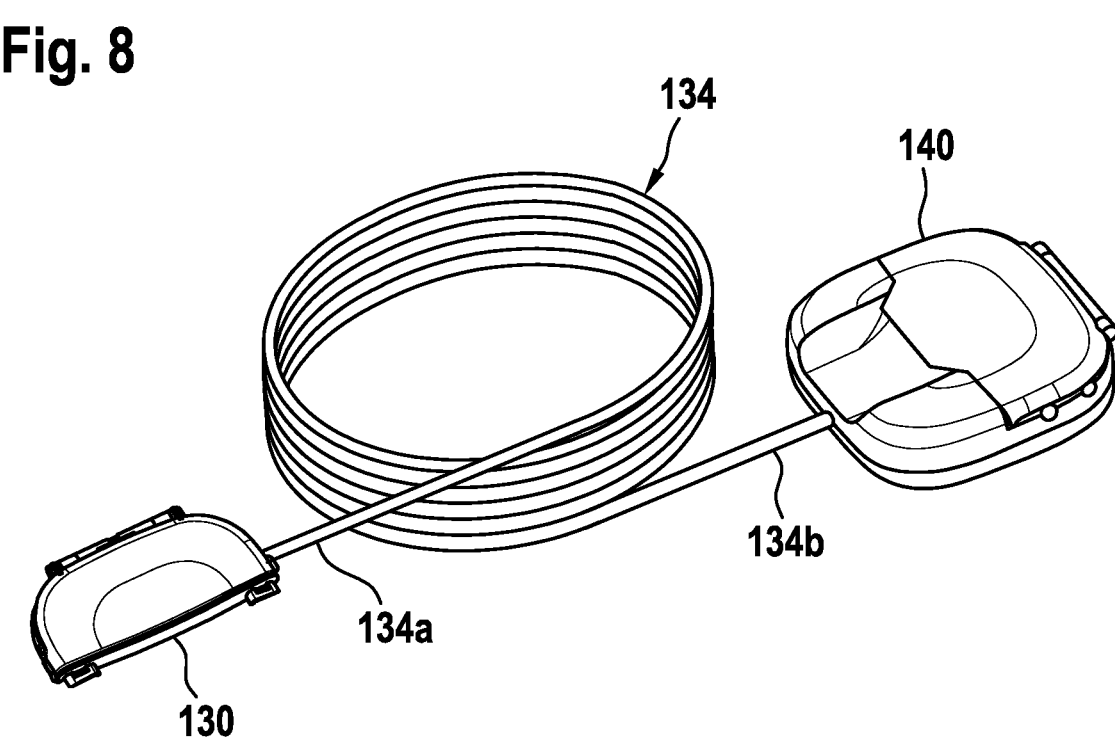
FIG. 8 shows a schematic view of a second lead interface module, and extension cable, and an electrode coupling box according to embodiments of the present disclosure.

FIG. 8 shows a schematic view of a second lead interface module 130, an extension cable 134, and an electrode coupling box 140 according to embodiments of the present disclosure.

The extension cable 134 may have a first end portion 132 fixedly or permanently connected to the second lead interface module 130 and a second end portion 134b connected to the electrode coupling box 140. The second end portion 134b may be permanently or detachably connected to the electrode coupling box 140.

In some embodiments, the extension cable 134 has a length of at least 1 m, preferable at least 1.5 m, and more preferably at least 2 m.

The second lead interface module 130 is connectable to the pulse generator module. The electrode coupling box 140 is connectable to the at least one neurological stimulation electrode. The at least one neurological stimulation electrode 10 may be permanently or detachably connected to the electrode coupling box 140. Neurological stimulation pulses generated by the pulse generator unit can be supplied to the at least one neurological stimulation electrode 10 via the second lead interface module 130, the extension cable 134, and the electrode coupling box 140.

Figure 9:
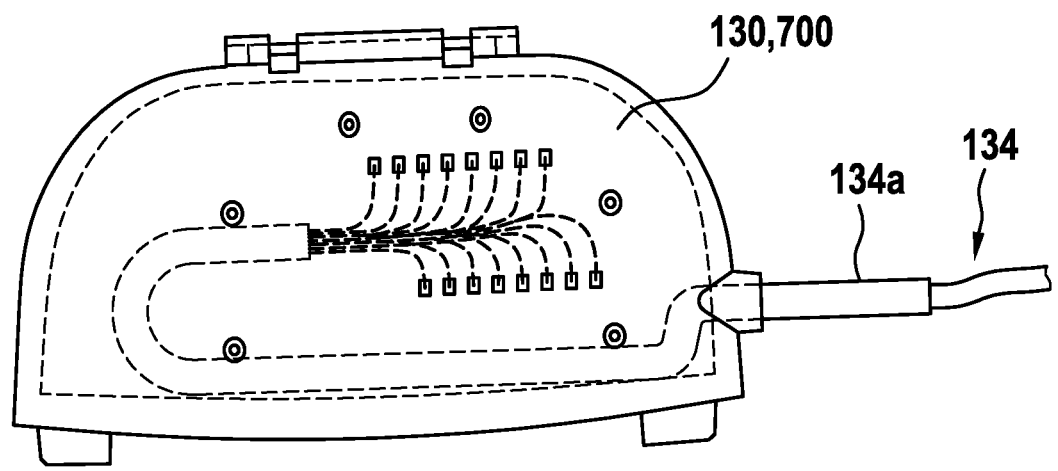
FIG. 9 shows a schematic view of the second lead interface module and a proximal end of the extension cable according to embodiments of the present disclosure.

FIG. 9 shows the second lead interface module 130 and the first or proximal end portion 134a of the extension cable 134.

The second lead interface module 130 may have a circuit board in an interior thereof. The circuit board may be configured similarly to the circuit board of the first interface module explained with respect to FIG. 5A. Therefore, a description of similar or identical aspects is not repeated.

The circuit board of the second lead interface module 130 may not have the U-shaped connection elements described with respect to FIG. 5A at the second side thereof. Instead, the plurality of connection elements at the second side of the circuit board may be solder pads. The extension cable 134 may be soldered to the solder pads. Accordingly, unlike the first lead interface module, the extension cable 134 is permanently connected to the second lead interface module and is not detachable.

Figures 10A, 10B:
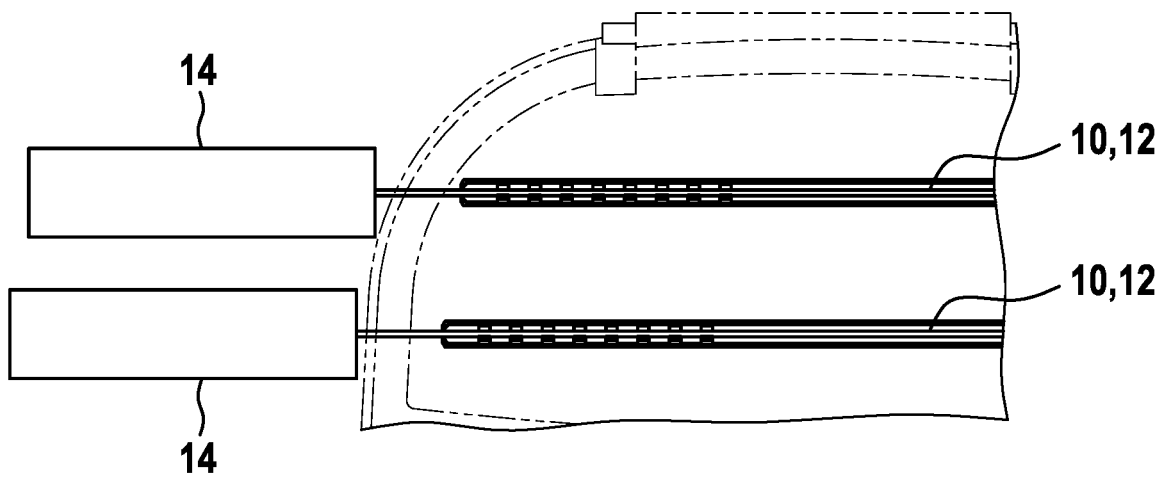
FIG. 10A shows a schematic view of an electrode coupling box according to embodiments of the present disclosure.
FIG. 10B shows a detailed view of a section of the electrode coupling box of FIG. 10A.

FIG. 10A shows a schematic view of an electrode coupling box 140 according to embodiments of the present disclosure. FIG. 10B shows a detailed view of a section of the electrode coupling box 140 of FIG. 10A.

The second or distal end 134b of the extension cable is connected to the electrode coupling box 140. Further, the at least one neurological stimulation electrode 10 may be permanently or detachably connected to the electrode coupling box 140. The electrode coupling box 140 may be configured to electrically connect the second or distal end 134b of the extension cable (and thus the second lead interface module and pulse generator module) and the at least one neurological stimulation electrode 10. Thereby, the neurological stimulation pulses generated by the pulse generator unit are transferred to the at least one neurological stimulation electrode 10 via the electrode coupling box 140.

In some embodiments, the electrode coupling box 140 may include a coupling box housing 142. The coupling box housing 142 may have one or more openings 144 to allow an entry of the at least one neurological stimulation electrode 10. In particular, an end portion 12 of the at least one neurological stimulation electrode 10 may be insertable into the electrode coupling box 140 via the one or more openings 144 to establish an electrical connection between the at least one neurological stimulation electrode 10 and the extension cable 134.

In some implementations, the at least one neurological stimulation electrode 10 may enter the electrode coupling box 140 at a first side thereof via the one or more openings 144. A stylet hub support 14 may be provided at a second side of the electrode coupling box 140 opposite the first side. From DDM:

The leads are hollow internally (have a lumen). Since the leads are very flexible the clinician needs a way to steer and locate the tips. For intraoperative use case only: the clinician inserts a stylet (metal wire) in the lumen of the lead and steers the lead distal end by controlling a plastic hub on the proximal end. The key here is that the IOC has to receive a lead with an already inserted stylet in its lumen and the stylet hub cannot interfere with the intraoperative testing.

In. FIG. 10A the stylet hubs or stylet hub supports 14 are outside the connector, used for steering lead. The channel spans the entire width of the device or electrode coupling box 140.

From GOP:

The stylet component is used in the placement of the stimulation electrodes within the patient, providing a semi-rigid 'guide wire' for the flexible lead to be steered into position. During intraoperative testing it is necessary that the neurological stimulation electrodes be placed in the electrode coupling box 140 without removing the stylets. During testing, if the leads require a placement revision for better therapy this can be easily achieved by opening the cover, revising the lead electrode position within the patient, then re-installing in coupling box 140.

The electrode coupling box 140, in particular the coupling box housing 142, may have an interior space having connection means therein configured to electrically connect the extension cable 134 and the at least one neurological stimulation electrode 10. For example, the connection means may include a plurality of connection elements, such as the U-shaped connection elements explained with respect to FIG. 6, which can be used to connect the extension cable 134 and the at least one neurological stimulation electrode 10 to each other.

For example, the at least one neurological stimulation electrode 10 or the end portion thereof can be inserted in a conductive channel formed by the plurality of connection elements. The plurality of connection elements can be soldered to a circuit board. Further, the extension cable 134 can be connected, for example soldered, to the circuit board such that an electrical connection e.g. between ring contacts of the at least one neurological stimulation electrode 10 and individual wires of the extension cable 134 can be established.

In some embodiments, the electrode coupling box 140 may be detachably connectable to the at least one neurological stimulation electrode 10, for instance by means of the U-shaped connection elements. Additionally, or alternatively, the extension cable 134 may be permanently connected to the electrode coupling box 140. For example, the extension cable 134 may be soldered to the circuit board which is located in the interior of the coupling box housing 142.

In some embodiments, the electrode coupling box 140 may have a lid similar or identical to the lid described with respect to the first lead interface module. In other embodiments, the electrode coupling box 140 does not have a lid but a fixed cover 700'.

In some embodiments, the fixed cover 700' may be made of a thermoplastic, such as a PC-ABS alloy. Additionally, or alternatively, the fixed cover 700' may be made of a transparent or semi-transparent material.

For example, the fixed cover 700' may be transparent or semi-transparent to allow a user to see the interior of the electrode coupling box 140, in particular an area in which the at least one neurological stimulation electrode 10 is connected to the electrode coupling box 140, in particular the circuit board.

According to some implementations, the coupling box housing 142 may include a recess or cavity 146 on a side, in particular an upper side, thereof. The recess or cavity 146 may be configured to accommodate a user's thumb. Accordingly, the user can firmly hold the electrode coupling box 140 e.g. during the insertion of the at least one neurological stimulation electrode 10 into the coupling box housing 142.

Figure 11:
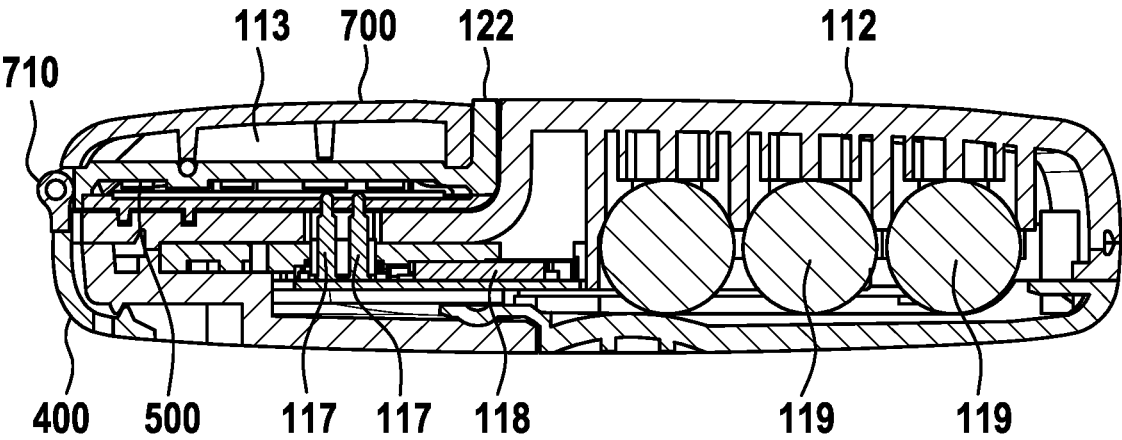
FIG. 11 shows a cross-sectional view of a pulse generator module with mated lead interface module according to embodiments of the present disclosure.
Figure 12:
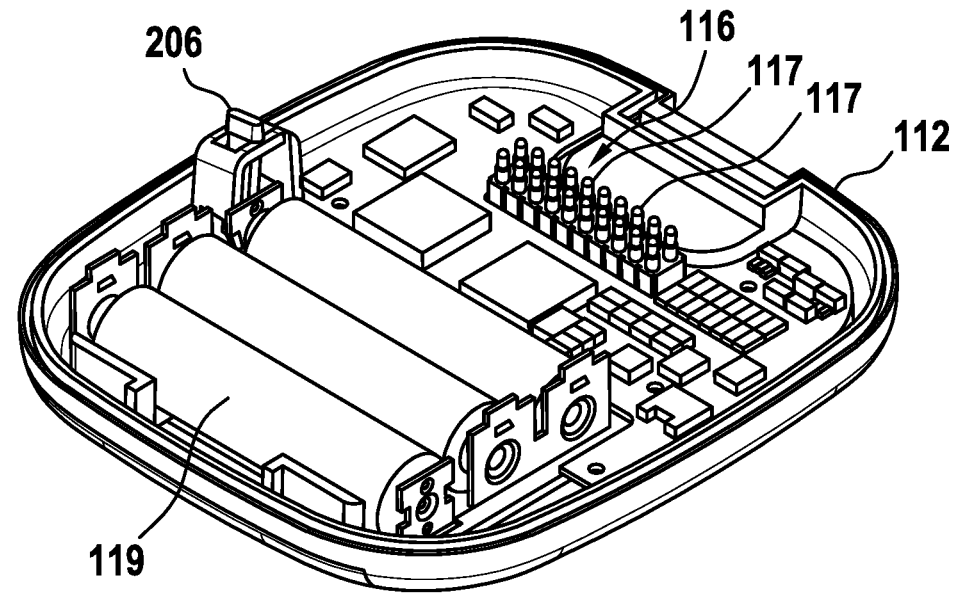
FIG. 12 shows a perspective view of an interior of a pulse generator module according to embodiments of the present disclosure.

FIG. 11 shows a cross-sectional view of a pulse generator module with mated first or second lead interface module according to embodiments of the present disclosure. FIG. 12 shows a perspective view of an interior of a pulse generator module according to embodiments of the present disclosure.

The lead interface module includes the circuit board 500 which may be arranged in the interior space 113 of the second housing 122 and may be connected to, or part of, the second electrical interface of the lead interface module which is connectable to the first electrical interface of the pulse generator module. The pulse generator module may have pulse generation circuitry 118.

The circuit board 500 may have a first side and a second side opposite the first side. The first side may face a bottom of the second housing 122, and the second side may face the open top portion of the interior space 113, in particular the lid 700.

Different portions of the second electrical interface can be located on the first side and the second side of the circuit board 500, and some parts of the second electrical interface can penetrate the circuit board 500 to connect the different portions of the second electrical interface.

In some embodiments, a first portion of the second electrical interface is exposed to an outside of the second housing 122 e.g. via one or more openings in the second housing 122, and a second portion of the second electrical interface is arranged in the interior space 113. The first portion may be configured to be electrically connected to the first electrical interface and the second portion may be configured to be (directly or indirectly) electrically connected to the at least one neurological stimulation electrode or an end portion thereof.

Preferably, the first portion of the second electrical interface is arranged at the first side of the circuit board 500 and the second portion of the second electrical interface is arranged at the second side of the circuit board 500 opposite the first side.

In order to electrically connect the second electrical interface to the first electrical interface 116 of the pulse generator module, the first electrical interface 116 of the pulse generator module may include a plurality of pins 117, such as male pins and/or pogo pins. For example, a number of the pins may be 16, 20 or more. The first portion of the second electrical interface may include a plurality of recesses or a plurality of pads, such as copper pads, on the first side of the circuit board 500 and configured to engage with the plurality of pins 117 of the first electrical interface 116 when the lead interface module is connected to the coupling portion.

In some embodiments, the pulse generator module may include one or more energy sources 119, such as batteries, in particular rechargeable and/or replaceable batteries.

According to some embodiments, which can be combined with other embodiments described herein, the pulse generator module may include a magnetic activation switch. For example, the pulse generator module may be switched on when a magnet, such as a permanent magnet, is brought into proximity of the magnetic activation switch and/or is moved in a particular direction. The pulse generator module may be switched off when the magnet is again brought into proximity of the magnetic activation switch and/or is moved in another direction.

In some embodiments, the pulse generator module may include at least one indicator 206 configured to indicate an operational state of the system. The at least one indicator 206 may be configured to indicate multiple patterns e.g. for "battery inserted", "RF/BLT association", "therapy active" and "magnetic activation".

The at least one indicator 206 may be a light source, such as an LED, preferably a single color LED.

According to some embodiments, which can be combined with other embodiments described herein, the pulse generator module may include a communication device configured for wireless communication. For example, the communication device may use RF and/or Bluetooth technology to wirelessly communicate with one or more external devices, such as remote devices. The one or more external devices may be provided to adjust therapy and/or collect patient feedback related to pain relief (e.g. surveys). Further, the pulse generator module 110 may autonomously collect statistics related to stimulation therapy usage patterns. These statistics can be telemetered from the pulse generator module 110 to the remote device using the communication device.

Figure 13:
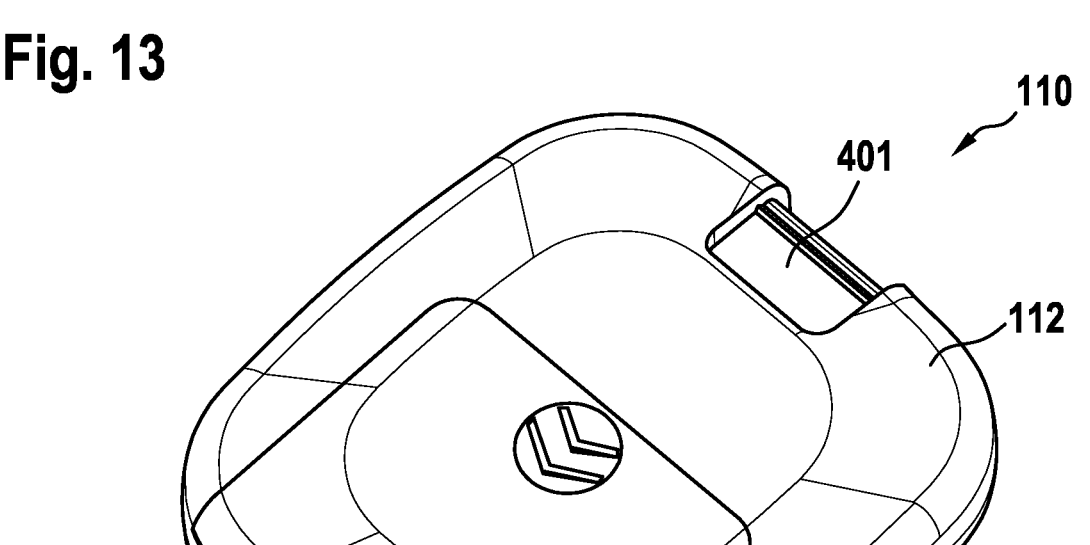
FIG. 13 shows a bottom view of a pulse generator module according to embodiments of the present disclosure.

FIG. 13 shows a bottom view of a pulse generator module 110 according to embodiments of the present disclosure.

In some embodiments, the pulse generator module 110 includes a space configured to accommodate the one or more energy sources, such as batteries. The space may be closed by a cover or door 112a. The cover or door 112a may be removeable to allow a user to access the space and replace the one or more energy sources.

In some implementations, one or more test points (not shown) configured for functional tests after production may be located in the space so as to be accessible when the cover or door 112a is removed.

FIG. 13 further illustrates a recess 401 which is configured to engage with the one or more clamps and/or one or more hinge elements configured to fix the lead interface module to the pulse generator module. The recess 401 may be a hinge "lip".

FIG. 14 shows a top view of a pulse generator module 110 and an interface cap 1400 according to embodiments of the present disclosure.

The interface cap 1400 may be connectable to the first electrical interface 116 when no lead interface module is mounted thereon to protect the first electrical interface 116 from dust, humidity and damage during cleaning and storage. The interface cap 1400 may be made of a semi-rigid material.

FIG. 14 further illustrates another embodiment of holding means configured to secure and/or retain the lead interface module once the lead interface module has been mounted to the coupling portion 114. In particular, the holding means may be configured to mechanically retain the lead interface module the lateral and rotational movement once secured.

The holding means may include at least one holding protrusion and at least one holding recess configured to engage with the at least one holding protrusion. The at least one holding protrusion 204' may be provided at the pulse generator module, and the at least one holding recess may be provided at the lead interface module. Alternatively, the at least one holding protrusion may be provided at the lead interface module, and the at least one holding recess may be provided at the pulse generator module.

In the example of FIG. 4, the least one holding protrusion 204' and/or the at least one holding recess have a circular shape.

The present disclosure provides a system which includes a reusable external pulse generator that supports multiple modes of use, namely intraoperative testing and patient-worn trialing. In particular, the same external pulse generator is connectable to two different lead interface modules, one of which can be used during intraoperative testing and another one which can be used during patient-worn trialing. This can reduce the cost of spinal cord stimulation therapies. Further benefits of the present disclosure are apparent from the following description and the accompanying drawings.

While the foregoing is directed to embodiments of the disclosure, other and further embodiments of the disclosure may be devised without departing from the basic scope thereof, and the scope thereof is determined by the claims that follow.

The invention claimed is:

1. A system (100) for neurological stimulation, comprising:
  (a) a pulse generator module (110), including:
    (i) a first housing (112) configured to accommodate a pulse generator unit, wherein the first housing (112) further includes a coupling portion (114); and
    (ii) a first electrical interface (116) located at the coupling portion (114), wherein the pulse generator unit is configured to generate neurological stimulation pulses to be supplied to at least one neurological stimulation electrode (10) via the first electrical interface (116);

(b) a first lead interface module (120) electrically connectable to the coupling portion (114) and the first electrical interface (116), wherein the first lead interface module (120) is detachably connectable to the at least one neurological stimulation electrode (10); and (c) a second lead interface module (130) connectable to the coupling portion (114) and the first electrical interface (116), wherein the second lead interface module (130) includes an extension cable (134) connectable to an electrode coupling box (140) for supplying the neurological stimulation pulses generated by the pulse generator unit to the at least one neurological stimulation electrode (10);

wherein at least one of the first lead interface module (120) and the second lead interface module (130) includes at least one first connection means (302) attachable to at least one second connection means (202) of the coupling portion (114);

wherein the at least one first connection means (302) and the at least one second connection means (202) provide a rotational axis for the respective lead interface module (120, 130) so that the respective lead interface module (120, 130) is connectable to the coupling portion (114) by means of a rotation of the respective lead interface module (120, 130) around the rotational axis; and wherein the rotational axis is arranged transverse to a direction of insertion of the respective lead interface module (120, 130) into the coupling portion (114).

2. The system (100) of claim 1, wherein:

the at least one first connection means (302) includes at least one protrusion and the at least one second connection means (202) includes at least one recess, or the at least one first connection means includes at least one recess and the at least one second connection means includes at least one protrusion.

3. The system (100) of claim 1, wherein at least one of the pulse generator module (110), the first lead interface module (120) and the second lead interface module (130) includes one or more clamps and/or one or more hinge elements (400) configured to fix the respective lead interface module (120, 130) to the pulse generator module (110) by means of a rotation of the one or more clamps and/or the one or more hinge elements (400).

4. The system (100) of claim 1, wherein the coupling portion (114) has a shape corresponding to an outer shape of the first lead interface module (120) and/or the second lead interface module (130) wherein the coupling portion (114) is formed as a cavity on the first housing (112).

5. The system (100) of claim 1, wherein at least one of the first lead interface module (120) and the second lead interface module (130) includes:

a second electrical interface (126, 136) electrically connectable to the first electrical interface (116); and a second housing (122, 132) having an interior space (113), wherein a first portion of the second electrical interface (126, 136) is exposed to an outside of the second housing (122, 132) and a second portion of the second electrical interface (126, 136) is arranged in the interior space (113), and wherein the first portion is configured to be electrically connected to the first electrical interface (116) and the second portion is configured to be electrically connected to the at least one neurological stimulation electrode (10).

6. The system (100) of claim 5, wherein the at least one of the first lead interface module (120) and the second lead interface module (130) includes a circuit board (500), and wherein the first portion of the second electrical interface (126, 136) is arranged at a first side of the circuit board (500) and the second portion of the second electrical interface (126, 136) is arranged at a second side of the circuit board (500) opposite the first side.

7. The system (100) of claim 5, wherein the first electrical interface (116) of the pulse generator module (110) includes a plurality of pins (117), and wherein the first portion of the second electrical interface (126, 136) includes a plurality of recesses or a plurality of pads configured to engage with the plurality of pins (117) of the first electrical interface (116) when the at least one of the first lead interface module (120) and the second lead interface module (130) is connected to the coupling portion (114).

8. The system (100) of claim 5, wherein the second portion of the second electrical interface (126, 136) includes a plurality of connection elements directly or indirectly connectable to the at least one neurological stimulation electrode (10).

9. The system (100) of claim 8, wherein the plurality of connection elements (600) of the first lead interface module (120), are arranged to define at least one conductive channel (C) having a length, wherein each conductive channel (C) is configured to receive a respective conductive device, wherein the conductive device is an end portion (12) of the at least one neurological stimulation electrode (10) or is connected to the at least one neurological stimulation electrode (10).

10. The system (100) of claim 9, wherein each connection element (600) of the plurality of connection elements comprises a U-shaped element having an open top portion (602), wherein the open top portion (602) is configured to allow an entry of the conductive device into an inside of the U-shape in a direction perpendicular to the length of the conductive channel (C).

11. The system (100) of claim 10, wherein the U-shape of the connection element (600) is such that the conductive device is held in the inside of the U-shape after the conductive device has been inserted.

12. The system (100) of claim 9, wherein each connection element (600) of the plurality of connection elements is formed by a piece of bent metal, wherein the metal is copper, beryllium copper, gold, or beryllium copper with a gold coating.

13. The system (100) of claim 9, wherein the plurality of connection elements (600) include at least one electrical connection element (602) configured to provide the electrical connection to the at least one neurological stimulation electrode (10) and at least one anchor element (606) electrically isolated from the at least one neurological stimulation electrode (10).

14. The system (100) according to claim 1, wherein the first lead interface module is not connectable to the second lead interface module, and wherein the second lead interface module is not connectable to the first lead interface module.

15. A system (100) for neurological stimulation, comprising:

(a) a pulse generator module (110), including:

(i) a housing (112) with a coupling portion (114); and (ii) a first electrical interface (116) at the coupling portion (114) configured to supply neurological stimulation pulses;

(b) a lead interface module (120, 130) mechanically and electrically connectable to the coupling portion (114), wherein the lead interface module (120, 130) includes:

(i) a second housing (122, 132) having an interior space (113);

(ii) a second electrical interface (126, 136) having a first portion arranged outside the second housing (122, 132) and a second portion arranged in the interior space (113), wherein the first portion is configured to electrically couple with the first electrical interface (116); and (iii) a plurality of connection elements (600) arranged in the interior space (113) and electrically connected to the second portion of the second electrical interface (126, 136), wherein each connection element (600) defines a respective conductive channel (C) configured to receive an end portion (12) of a neurological stimulation electrode (10);

wherein the lead interface module (120, 130) is detachably connectable to the coupling portion (114) by engagement of at least one connection means (302) of the lead interface module (120, 130) with at least one complementary connection means (202) of the coupling portion (114);

wherein the at least one connection means (302) and the at least one complementary connection means (202) provide a rotational axis for the lead interface module (120, 130) so that the lead interface module (120, 130) is connectable to the coupling portion (114) by means of a rotation of the lead interface module (120, 130) around the rotational axis; and wherein the rotational axis is arranged transverse to a direction of insertion of the lead interface module (120, 130) into the coupling portion (114).

16. The system (100) of claim 15, wherein each connection element (600) of the plurality of connection elements comprises a U-shaped element having:

an open top portion (602) configured to allow entry of the end portion (12) of the neurological stimulation electrode (10) into an inside cavity (603) of the U-shaped element in a direction substantially perpendicular to a length axis of the conductive channel (C); and inwardly bent legs (605) configured to provide a clamping force to retain the end portion (12) within the inside cavity (603) after insertion.

17. The system (100) of claim 15, wherein the second electrical interface (126, 136) includes a circuit board (500), and wherein the first portion of the second electrical interface (126, 136) is disposed on a first side of the circuit board (500) and the second portion of the second electrical interface (126, 136) is disposed on a second side of the circuit board (500) opposite the first side.

18. A system (100) for neurological stimulation, comprising:

(a) a pulse generator module (110) including:

(i) a housing (112) having a coupling portion (114) formed as a cavity or recess;

(ii) a first electrical interface (116) located within the coupling portion (114) and including a plurality of electrical pins (117); and (iii) pulse generation circuitry (118) configured to generate neurological stimulation pulses;

(b) a first lead interface module (120) selectively attachable to the coupling portion (114), wherein the first lead interface module (120) includes:

(i) a body portion shaped complementary to the coupling portion (114);

(ii) a second electrical interface (126) including a plurality of receptacles configured to receive the plurality of electrical pins (117) when the first lead interface module (120) is connected to the coupling portion (114);

(iii) a plurality of U-shaped connection elements (600), each U-shaped connection element (600) having an open top portion (602) and being configured to receive and retain an end portion (12) of a neurological stimulation electrode (10);

(iv) at least one first connection means (302) attachable to at least one second connection means (202) of the coupling portion (114), wherein the at least one first connection means (302) and the at least one second connection means (202) provide a rotational axis for the first lead interface module (120) so that the first lead interface module (120) is connectable to the coupling portion (114) by means of a rotation of the first lead interface module (120) around the rotational axis, wherein the rotational axis is arranged transverse to a direction of insertion of the first lead interface module (120) into the coupling portion (114); and (v) at least one mechanical retention feature (400) configured to secure the first lead interface module (120) to the pulse generator module (110);

(c) a second lead interface module (130) selectively attachable to the coupling portion (114) as an alternative to the first lead interface module (120), wherein the second lead interface module (130) includes:

(i) a third electrical interface (136) electrically connectable to the first electrical interface (116); and (ii) an extension cable (134) permanently connected to the third electrical interface (136) and connectable to an electrode coupling box (140);

wherein only one of the first lead interface module (120) and the second lead interface module (130) is connectable to the coupling portion (114) at any given time.

19. The system (100) of claim 18, wherein the at least one mechanical retention feature (400) comprises one or more clamps, hinges, or snap-fit elements rotatable or movable to interlock the first lead interface module (120) with the pulse generator module (110).

20. The system (100) of claim 18, wherein the first lead interface module (120) includes a lid (700) rotatably connected to the body portion, the lid (700) being movable between:

an open position that permits insertion or removal of the end portion (12) of the neurological stimulation electrode (10) into the plurality of U-shaped connection elements (600); and a closed position that secures the end portion (12) within the plurality of U-shaped connection elements (600).

* * * * *